(12) United States Patent
Helm et al.

(10) Patent No.: US 7,488,302 B1
(45) Date of Patent: Feb. 10, 2009

(54) DEVICE ALLOWING SERIAL USE OF CLEAN AND ALTERNATIVE BLOOD FILTERS DURING BLOOD FILTRATION

(76) Inventors: Robert Helm, P.O. Box 656 215 S. Rd., Rye Beach, NH (US) 03871; Richard Herink, 768 Bingham Rd., Ridgewood, NJ (US) 07450

( * ) Notice: Subject to any disclaimer, the term of this patent is extended or adjusted under 35 U.S.C. 154(b) by 451 days.

(21) Appl. No.: 10/907,290

(22) Filed: Mar. 28, 2005

Related U.S. Application Data

(60) Provisional application No. 60/521,301, filed on Mar. 29, 2004.

(51) Int. Cl.
*A61M 37/00* (2006.01)

(52) U.S. Cl. ............... 604/6.09; 604/6.1; 604/6.11; 604/6.13; 422/44; 422/45; 422/48

(58) Field of Classification Search ............ 604/4.01, 604/5.01, 5.04, 6.09, 6.1, 6.11, 6.13; 210/645, 210/200, 201, 203, 255, 253, 254, 500.21; 422/44, 48

See application file for complete search history.

(56) References Cited

U.S. PATENT DOCUMENTS

| | | | | |
|---|---|---|---|---|
| 3,802,432 A | * | 4/1974 | Djerassi | 604/6.03 |
| 4,828,543 A | * | 5/1989 | Weiss et al. | 604/6.09 |
| 5,085,049 A | * | 2/1992 | Rim et al. | 60/274 |
| 5,282,783 A | * | 2/1994 | Lindsay | 604/6.09 |
| 6,187,530 B1 | * | 2/2001 | Scholin et al. | 435/4 |
| 6,451,257 B1 | | 9/2002 | Flamer | 422/44 |
| 6,613,008 B2 | | 9/2003 | Aboul-Hosn et al. | 604/5.01 |
| 2003/0212433 A1 | | 11/2003 | Ambrisco et al. | 606/200 |

\* cited by examiner

*Primary Examiner*—Leslie R Deak
(74) *Attorney, Agent, or Firm*—Heslin Rothenberg Farley & Mesiti P.C.

(57) ABSTRACT

A device that allows for serial (time) use of clean blood filters during the use of a heart lung machine. The device is comprised of a series of filters and a switching mechanism that allows the new filter to be placed in the blood flow pathway while at the same time removing the old (previous) filter. A clean filter is always available, and filters for specific components of blood or those able to bind and remove specific biochemicals can be used.

11 Claims, 6 Drawing Sheets

DEVICE ALLOWING SERIAL USE OF CLEAN AND ALTERNATIVE BLOOD FILTERS DURING BLOOD FILTRATION

This application is related to provisional application 60/521,301 filed Mar. 29, 2004.

This invention relates to the improvement of continuous flow circuit blood filtration. During standard blood filtration, a blood filter is placed in the line of return blood flow to the body to remove unwanted elements including both cellular and non-cellular matter. Use of such a single in-line arterial filter is the present standard for blood filtration during such uses as cardiopulmonary bypass for cardiac surgery. A drawback to the single filter filtration system is that as filtration time progresses, the filter apparatus becomes progressively covered with filtrate, yet blood flow must continue through this apparatus until the end of the filtration period. As blood flows into and past filtered matter, the mechanical effect of this flow can serve to degrade this cellular and non-cellular filtrate, releasing smaller particles and chemically active substances into the filtered blood. Pressure increase resulting from filter material blocking previously open channels serves to increase the mechanical damage that is inflicted upon this filtered material.

One of the main objections to the use of the heart lung machine (used here as an example of a system that employs an arterial blood filter) is that its use leads to a whole body inflammatory response and significant physiologic derangements that ultimately can lead to multi-organ dysfunction and neurocognitive defects. Great effort has been expended in trying to optimize all components of the heart-lung machine in order to minimize these adverse sequelae. Biocompatible coating of internal surfaces of the heart lung machine, minimizing the size of the heart lung apparatus (and therefore the magnitude of the surface exposure), the use of less traumatic centrifugal pumps, and the incorporation of hollow fiber membrane oxygenators, are examples of technical advancements that have served to decrease the physiologic insult of the heart-lung apparatus. In addition, pharmacologic agents such as aprotinin (Trasylol) have been developed that also act to block or attenuate the activation of the body's inflammatory response system. Taken as a whole, these technical and pharmacologic advances serve to (1) decrease direct mechanical trauma to the blood and its components, and (2) decrease the amount of activation of active blood cellular elements such as white cells and platelets. The net effect of these two actions is (1) a decrease in particulate and cellular debris, and (2) decrease in the reactive biochemicals released by these abnormally activated and damaged tissues and cells. Nevertheless, despite these advances, cellular trauma and activation (with the release of potentially harmful particulate matter and chemical mediators) continues to occur. In fact, an entire industry ("off-pump" heart surgery) has emerged and rapidly grown based upon the basic concept of avoiding the use of the heart-lung machine. Today, at some centers, as many as 98% of coronary bypass operations are performed using the off-pump technique, despite its increased difficulty, and unknown mid and long-term results. A majority of institutions still uses the heart-lung machine for a majority of their coronary artery bypass procedures, however, and this heart-lung machine is absolutely required for all procedures where entry into the heart chambers is required such as during valve surgery. Therefore, it remains essential that efforts continue to optimize the heart-lung machine.

During use of the heart lung machine, the primary "standard" mechanism for removing particulate and cellular debris (resulting from body's interaction with the heart-lung machine as well as from tissue and other particulate debris released by the surgical procedure itself) from the circulation is the placement of a single blood filter in the arterial line prior to returning the blood to the patient. While this single filter mechanism does serve to remove particulate matter, a major drawback is that the filtered "unwanted" debris/material remains in the path of blood flow and is continuously washed by this flow, causing continuous hydrostatic injury to the trapped debris. There are several adverse consequences of utilizing this standard single filter system in blood flowing from and then into the human body: (1) the filter becomes coated over time leaving less open channels so that the pressure required to maintain constant flow increases thus leading to an increase in damaging hydrostatic forces, (2) continued hydrostatic mechanical injury/impact upon the trapped particulate matter serves to break this material into smaller particles that then may be able to pass through the filter and into the body, and (3) much of the filtered material consists of whole cells and or cellular debris which has enormous biochemical potential, and the continued bombardment of this cellular material serves to release the active substances into the body. These three adverse effects are progressive and compounding: the longer the blood is filtered, the more filtered cellular and non-cellular material builds up on the filter mechanism, and the greater the pressure placed upon the trapped/filtered matter, and the greater the mechanical release of injurious particulate and chemically active matter.

The prior art includes U.S. Pat. No. 6,613,008 to Aboul-Hosn, et al which discloses an integrated system for cardiopulmonary bypass surgery. More specifically the patent discloses an improved cardiopulmonary bypass system which consolidates and miniaturizes the entire CPB system and which includes an arterial filter.

U.S. Pat. No. 6,451,257 to Flamer illustrates the structure of an improved arterial blood filter device for use during cardiovascular surgery and discusses various patents constituting the prior art.

Patent Publication U.S. 2003/0212433 discloses an adjustable blood filtration device for use in cardiac surgery.

A solution to the above-delineated drawbacks of a single arterial filter system is to utilize not a single filter for the entire blood flow period, but to use multiple filters applied in a temporally serial fashion. This invention utilizes a single filter for a period of time. At the end of this time period the invention allows that this first filter is taken off line and that blood flow is then re-directed to a new (second) filter. This process is repeated (i.e., third, fourth, etc. filters) until the end of the blood flow period. This invention provides significant benefit to the patient (e.g. the patient undergoing open-heart surgery utilizing the heart-lung machine) by removing filtered "unwanted" debris from the blood pathway (by removing the used filter after a period of time) thereby reducing hydrostatic injury to this debris. Objects of this invention include providing a device to (1) improve flow dynamics of the heart lung apparatus by providing a clean filter with more open channels, (2) avoid the continued breakdown and release of filtered debris into the blood (in smaller particulate form) which results from continued high pressure blood flow into this debris, and (3) avoid the continued release of bioactive chemicals from the filtered material which results from the same hydrostatic injury.

Accordingly, an object of this invention is to provide a new and improved device for the filtration of blood in connection with a heart-lung machine or other extracorporeal circulation device.

Another object of this invention is to provide a new and improved multiple filter device to minimize or eliminate the problems associated with filtrate in a heart-lung machine or other extracorporeal circulation device.

A further object of this invention is to provide a new and improved device for serial use of clean blood filters during blood filtration when using a heart-lung machine or other extracorporeal circulation device.

A further object is to provide a new means of introducing multiple different types of blood filters (e.g. leukocyte filters, complement binding filters) "on demand" while utilizing the heart-lung machine or other extracorporeal circulation device. This will allow for fine alterations of the blood through the ability to: (1) apply any type of desired filter, (2) initiate use of this filter at any time point during use of the heart lung machine, (3) maintain this filter's use for any desired period of time, and (4) use this filter in any desired combination with other type(s) of blood filters (both parallel and serial).

The above and other objects and advantages of the present invention may be more clearly seen when viewing in conjunction with the accompanying drawings wherein.

Figure 1:
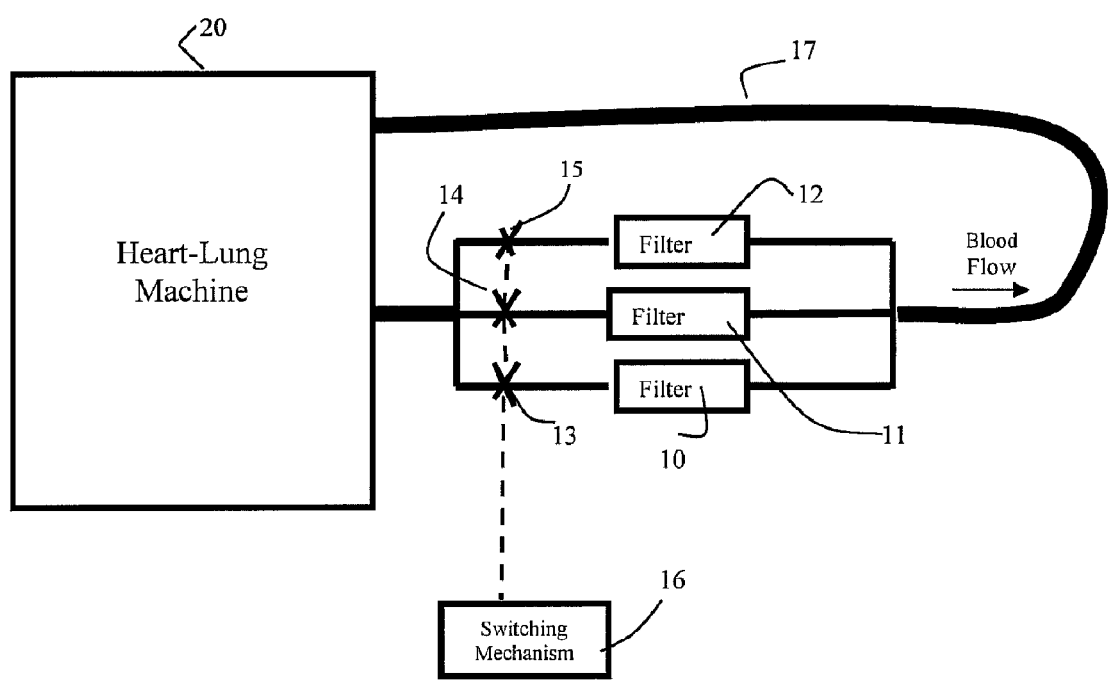
FIG. 1 is a schematic view of the invention showing the multiple parallel filters which can be brought on line in a temporally serial manner.

Referring now to the drawings, FIG. 1 demonstrates how this invention proposes to use multiple filters in a temporally serial fashion. The filters 10, 11 and 12, can be switched at various time intervals by a switching mechanism 16 each coupled to related flow control valves 13, 14 and 15 respectively. The filters are located in a parallel arrangement in a blood flow line 17 from the heart-lung machine 20. In order for blood flow to continue as a first operative filter 10 becomes progressively covered with filtrate the flow is switched by switching mechanism 16 to filter 11 by opening valve 14 and closing valve 13. Valve 15 remains closed until filter 11 is also covered with filtrate. Then valve 15 is opened and valve 14 is closed, directing the blood flow to the filter 12. The filters not in use can be replaced while the blood flow continues uninterrupted. Different type filters can also be used as previously noted.

Figure 2:
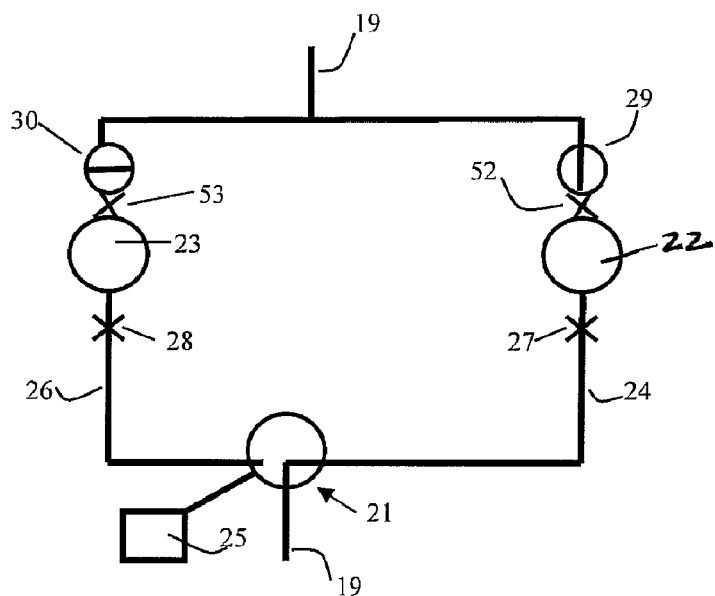
FIG. 2 is a schematic view of the invention showing filters in a parallel arrangement wherein the flow is regulated by an in flow valve switching mechanism. This switching mechanism can be controlled manually or by a time, pressure, flow or particulate matter sensing transducing device.

FIG. 2 shows an embodiment wherein the flow in line 19 from a heart lung machine 20 is directed to a two-way valve 21. Filters 22 and 23 are located in parallel lines 24 and 26 respectively and either one or the other receives flow from the two-way valve 21. As shown in FIG. 2, the flow is directed to line 24 and filter 22. A manual sensor or time based control mechanism 25 activates valve 21 opening in one direction to line 26 and closing to line 24. Manual clamps 27 and 28 or one-way valves 29 and 30 can be placed on lines 24 and 26 respectively to prevent leaching of bioactive material from the excluded filter into the downstream flow. Similarly, clamps 52 and 53 can be placed downstream of filters 22 and 23.

Figure 3:
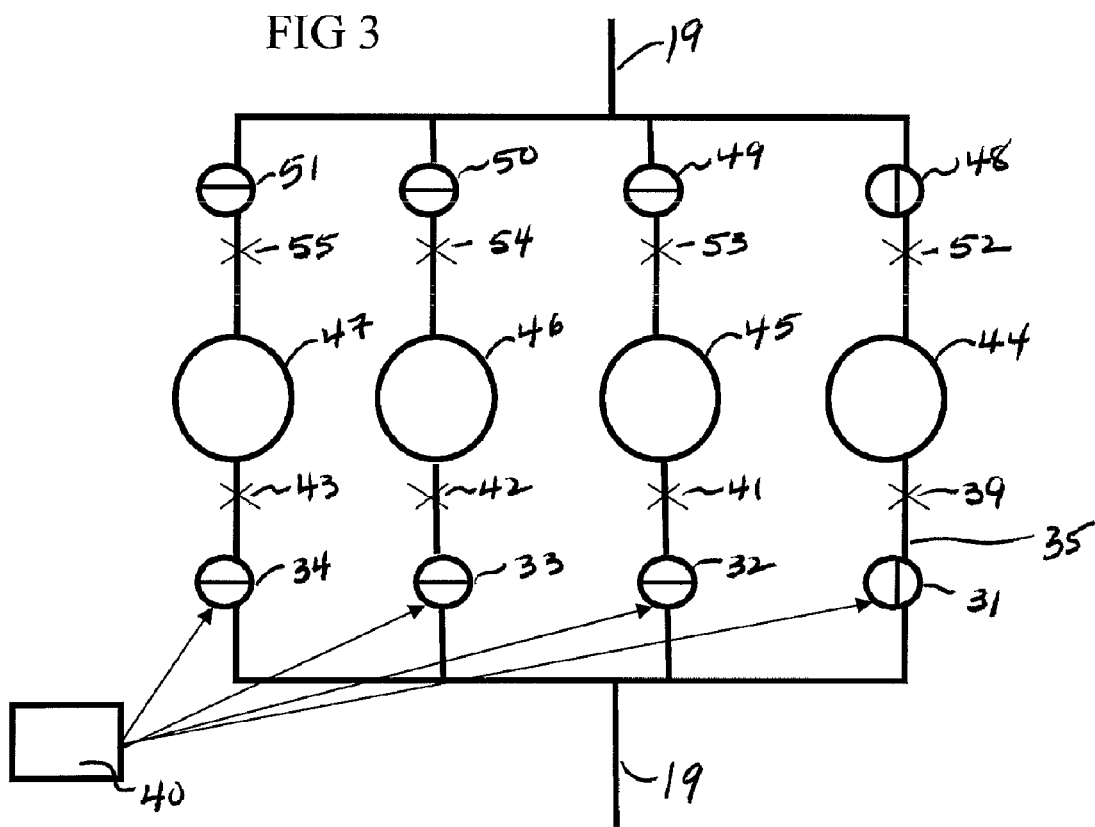
FIG. 3 is a schematic view of an embodiment of the invention wherein a plurality of parallel filters are each controlled by a corresponding in flow valve controlled manually or by a time, pressure, flow or particulate matter sensing transducing device.

FIG. 3 illustrates an arrangement wherein separate valves 31, 31, 33 and 34 are located in separate parallel lines 35-38 and controlled by timer 40 or other manual or sensor based control mechanism. Valve 32 is shown as open in FIG. 2. Each line 35-38 can include a manual secondary flow control device in the form of a line clamp 39, 41, 42 43 and/or one-way valve 48, 49, 50, and 51. Clamps can also be applied downstream to prevent leaching of bioactive material into the downstream flow.

Figure 4:
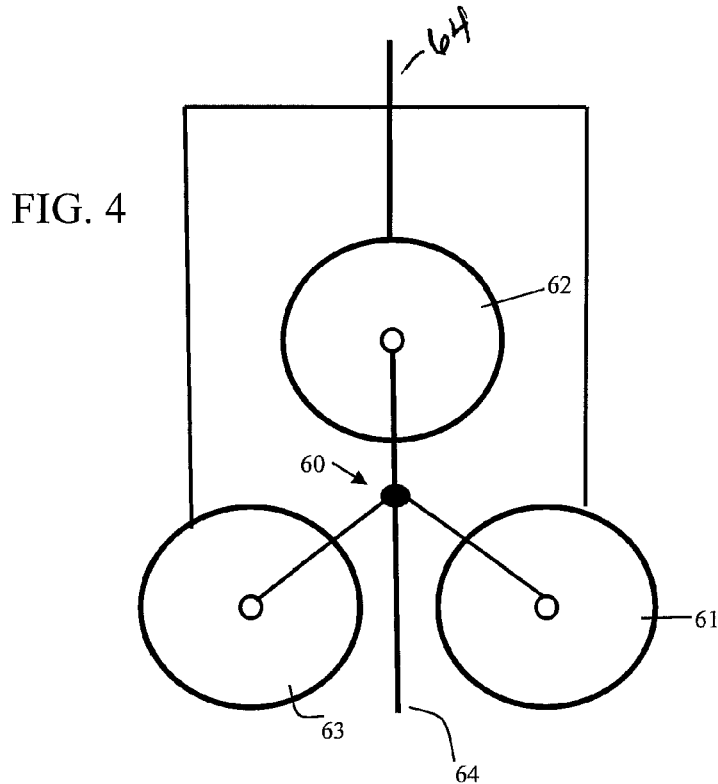
FIG. 4 is a schematic view of an embodiment of the invention utilizing a three-way valve to direct flow to one of three filters at any time during use of the heart lung machine. The multiple filters are arranged in a circular fashion around a central input channel and flow control valve.

FIG. 4 illustrates the invention using a three-way valve 60 with filters 61, 62 and 63. The flow along line 64 passes serially through filter 61 then 62 and then 63 on a timed basis. The remaining elements in this embodiment are similar to the elements in FIGS. 2 and 3, including the possibility of manual control with line clamps (not shown). As in the other embodiments, switching between filters is controlled manually or by a timing, pressure, flow or particulate sensor.

Figure 5A:
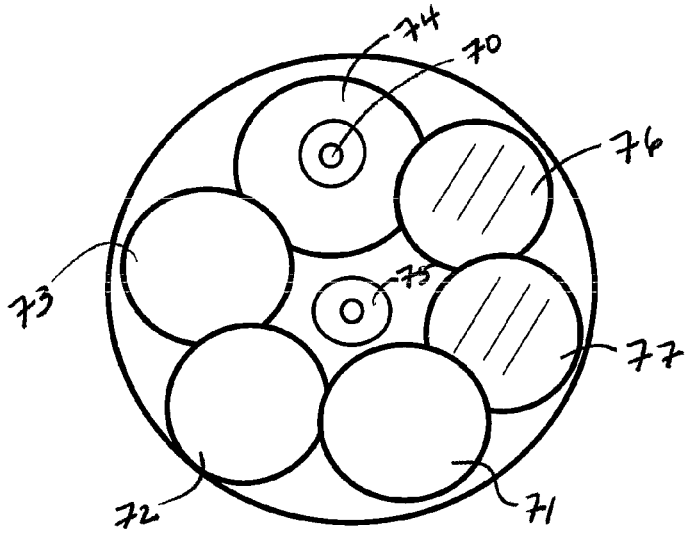
FIGS. 5a and 5b depict a filter arrangement where single input and output channel are eccentrically placed leading to and from a circular group of filters arranged around a central rotating mechanism. In this embodiment, the single input and output lines remain stationary and the new filters are temporally serially rotated/moved into line with the input and out channel.

FIG. 5a illustrates in a front view the embodiment of the invention where the single input and output line 70 remains fixed/static, while the new/clean blood filters 71, 72 and 73 are rotated into position by central rotating mechanism shaft 75 between the input and output lines and therefore into the line of the blood flow. Filter 74 is shown in use while filters 76 and 77 represent used filters which have been rotated off-line. This arrangement has the advantage of limiting the amount of dead-space volume in the whole of the filtration apparatus. The filters are rotated around in a central axial mechanism. While six are depicted, any number of filters could be placed on/in the rotating disc apparatus.

Figure 5B:
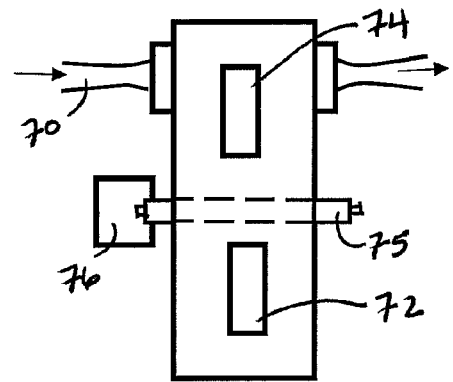

FIG. 5b is a side view of the embodiment of FIG. 5a showing the rotation control mechanism 76 and drive shaft 78. Filter 74 is shown in use while filter 72 is in reserve to be rotated in place.

Figure 6:
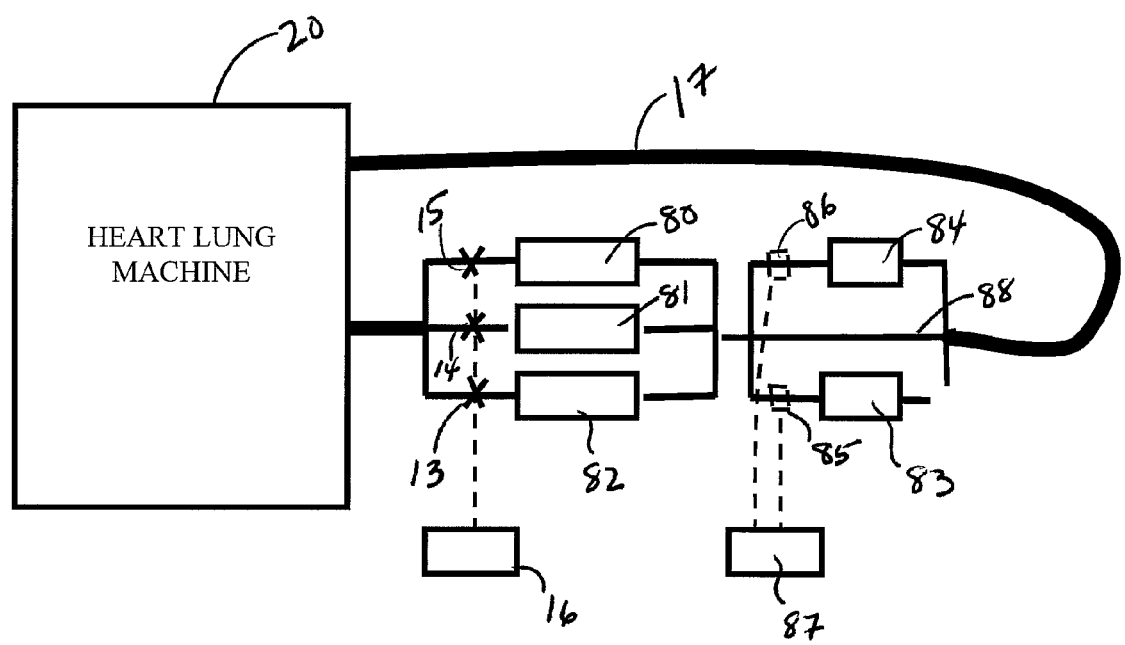
FIG. 6 is a schematic view showing target specific blood filters (e.g. leukocyte filter) placed in serial fashion to the first set of general blood filters depicted in FIGS. 1-4) allowing independent switching on and off line of these filters.

FIG. 6 is a schematic of a filtration system employing both a set of primary arterial filters 80, 81 and 82 as well as a set of downstream secondary target specific filters 83 and 84 (e.g., leukocyte, complement binding). In this embodiment, the secondary filters can be switched on or off line by valves 85 and 86 with control 87 at any desired time, or they can be bypassed by the central line 88. The remaining elements of this embodiment are similar to FIGS. 2 and 3, including the ability to manually place occlusive line clamps.

Figure 7:
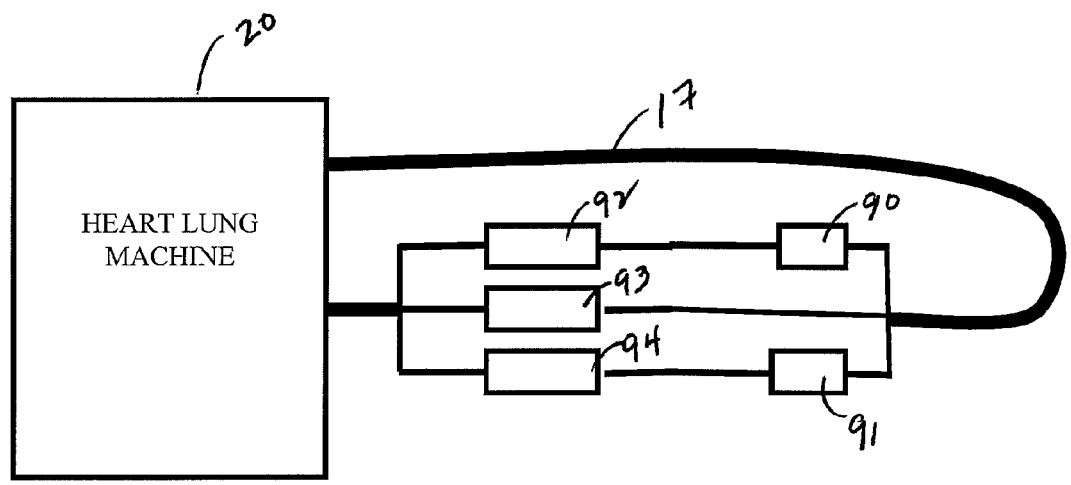
FIG. 7 is a schematic view showing serial placement of target specific filters with the target specific filters linked serially to individual general filters, allowing the general and target specific filters to be switched on and off line as a single unit.

FIG. 7 is a schematic depicting secondary filters with each secondary filter integrated with a primary arterial filter 92, 93, or 94. The individual primary and secondary filter units are switched on and off line at the desired time/point during extracorporeal circulation. The remaining elements of this embodiment which are not shown are similar to FIGS. 2 and 3 including the ability to manually place occlusive line clamps.

Figure 8:
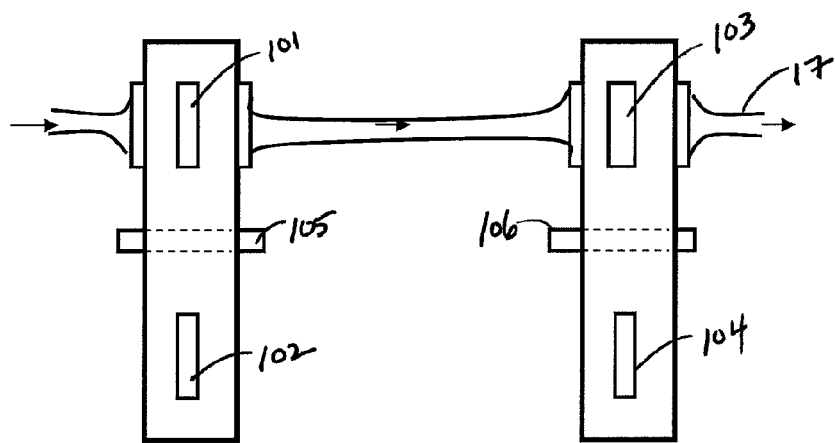
FIG. 8 is an alternate embodiment of the invention

FIG. 8 is a side view of a two filter disc mechanism with the upstream filters 101 and 102 each comprising a general blood filter and the secondary downstream filters 102 and 103 comprising target specific filters. The drive shafts 105 and 106 rotate filters 102 and 104 into position when the filters 101 and 103 require changing.

Figure 9:
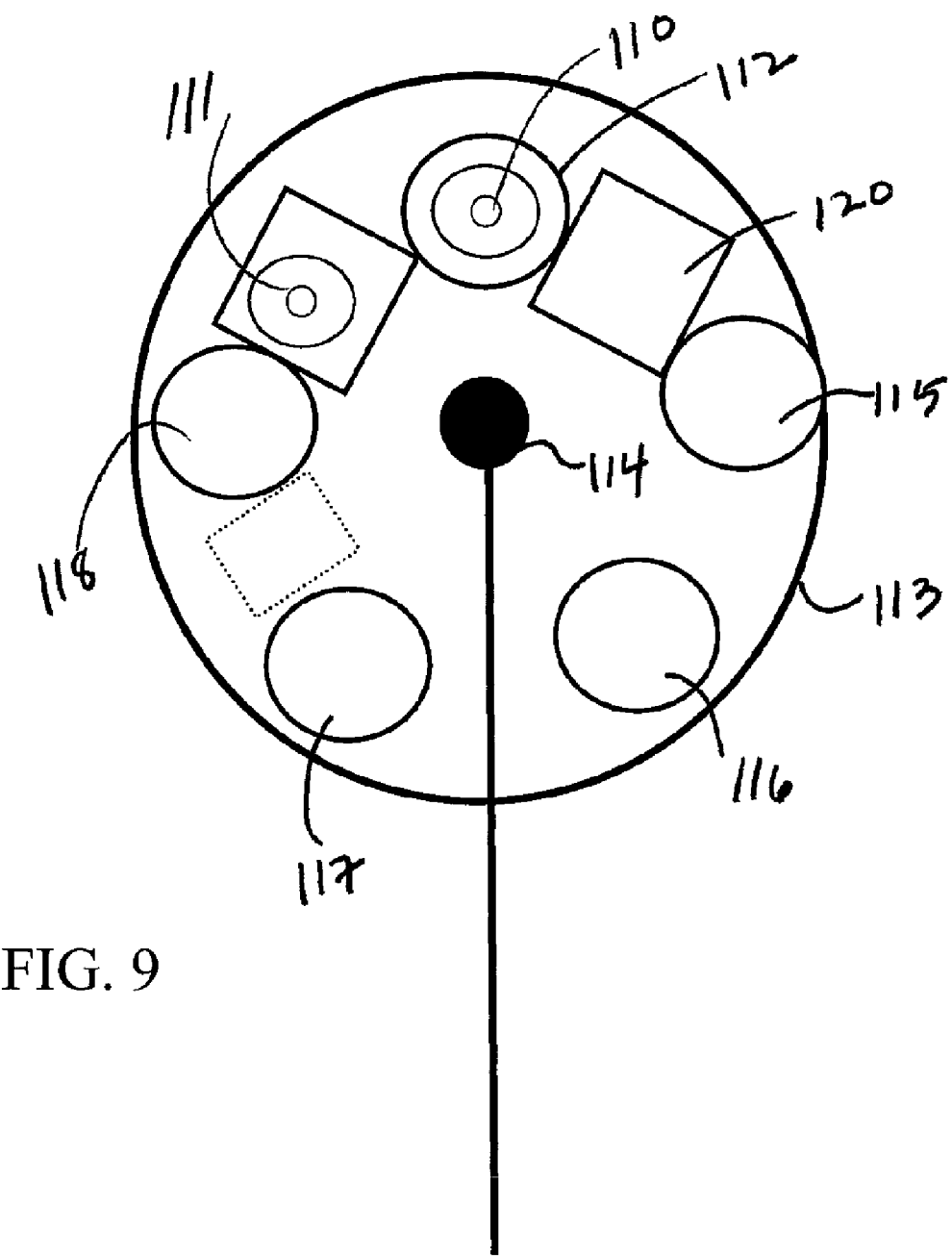
FIG. 9 is an alternate embodiment of the invention where two identical fixed eccentric lines are attached by a sealing/gasket mechanism to a multi-filter disc, which rotates around a central axis when the filter currently in use has reached its filtration limit.

FIG. 9 is a further embodiment of the invention wherein two identical fixed eccentric input lines 110 and 111 and output lines are attached by a sealing gasket mechanism 112 to a multi-filter disc 113 which rotates about a central axis 114. When the filter 110 currently in use has reached its filtration limit according to a predetermined parameter such as time, pressure, flow or particulate build-up, the multi-disc filter 113 is rotated clockwise. The new filter 111, a previously off-line filter line 115, 116, and 117 is rotated to the on-line position. The used filter 110 is rotated off-line to an area between the filters 120. By having input/output lines approximately offset, a normal flow through filters is always maintained. This embodiment is preferable for a roller type pump.

This invention has several other potential beneficial applications in respect to blood filtration. First, there have become available many different types of blood filters. These include filters specific for (1) the different cellular components of blood such as leukocytes (white blood cells), as well as (2) filters that can bind and remove biochemicals such as enzymes and hormonal messengers and other bioactive chemicals. As the body's reaction to the foreign surface and manipulations of the heart lung machine is a dynamic process, using this invention these various types of filters could be brought in-line at specific time periods in the blood filtration process to maximize their effectiveness and optimally improve patient outcome. These target specific filters would be brought in line in series with the presently active in-line standard arterial filter. This in series arrangement of target specific filters is depicted in FIG. 5

An example of the use of this invention for specific cellular filtration can be illustrated using leukocyte specific filtration. If leukocytes—the primary cellular mediators of inflammation—are most active and found in highest concentration during the first fifteen minutes of filtration, the invention could place a leukocyte filter in line during minutes 0-15 to remove these reactive cells at this peak time. By removing these highly reactive and secretory cells, their inflammatory sequelae would be minimized. FIGS. 6, 7, 8 demonstrate leukocyte filters placed in line downstream (serially) from the set of primary arterial filters. These individual filters can be brought on or off line at any time during the case to selectively remove unwanted blood elements and/or active biochemicals.

As stated, another alternative use for this invention would be to selectively bind and remove unwanted biochemicals secreted by the body during exposure to the heart lung machine. An example would be a filter that could be introduced at a specific time during the time period of heart-lung bypass that would bind and remove from the circulation a specific inflammatory biochemical messenger known as complement C3a. This mediator has known deleterious effects and its removal from the blood stream would provide patient benefit by decreasing the adverse sequelae induced by this potent chemical messenger. FIGS. 6, 7, 8 demonstrate complement binding filters placed downstream from the set of primary arterial filters. In FIG. 8, the second filter bank (downstream) is identical to the primary arterial filter bank except for the type and possibly number of filters.

An essential point regarding this invention is that for the first time a device would become available that could help to optimize the patients blood in a dynamic way by specifically and permanent removing harmful cellular and chemical elements. Both the standard particulate filters, as well as target specific filters could be introduced and changed at any particular point in time desired (actual timing and use of the individual filters would be based on the supportive scientific literature).

While the invention has been explained by a detailed description of certain specific embodiments, it is understood that various modifications and substitutions can be made in any of them within the scope of the appended claims which are intended also to include equivalents of such embodiments.

What is claimed is:

1. A continuous blood filtration system for cardiac surgery involving a heart lung machine comprising:
   a line for the continuous circulation of blood for filtration comprising a first fixed input line and output line pair for the circulation of blood to the heart lung machine;
   a first carrier having a plurality of blood filters fixedly arrayed relative to each other thereon and moveable with respect to the first input and output line pair so as to selectively position individual ones of said blood filters in sealing engagement with the first input and output lines so as to permit blood to flow through a selected filter.

2. A continuous blood filtration system in accordance with claim 1 wherein:
   the heart lung machine comprises a centrifugal pump based heart lung machine; and
   further including a control mechanism to move said carrier.

3. The system of claim 1 wherein the filters comprise multiple different types of blood filters.

4. The system of claim 3 wherein the filters include at least one leukocyte filter.

5. The system of claim 3 wherein the filters include at least one biochemical filter.

6. A method of using the system of claim 3 comprising the following steps:
   determining a time period during a cardiac surgery when an unwanted substance in the blood is in relatively high concentration; and
   moving a target-specific filter for that substance into engagement during said time period.

7. The system of claim 1 further comprising a control means for moving the carrier upon the happening of a predetermined event so as to move one filter out of engagement and another filter into engagement.

8. The system of claim 1 further comprising multiple input line and output line pairs and corresponding filter carriers, each of which is independently moveable with respect to its corresponding input line and output line pair.

9. The system of claim 8 wherein at least one carrier comprises multiple general and target-specific blood filters.

10. A method of using the system of claim 9 comprising the following steps:
    determining a time period during a cardiac surgery when an unwanted substance in the blood is in relatively high concentration; and
    moving a target-specific filter for that substance into engagement during said time period.

11. The system of claim 1 wherein the carrier has substantially the shape of a disc with an axis of rotation and wherein the movement of the disc is rotational, substantially about that axis.

* * * * *